United States Patent [19]

Bräunling et al.

[11] Patent Number: 4,733,012

[45] Date of Patent: Mar. 22, 1988

[54] PROCESS FOR THE PREPARATION OF 4-HALOMETHYLBENZALDEHYDE

[75] Inventors: Hermann Bräunling; Dieter Kippe, both of Burghausen, Fed. Rep. of Germany

[73] Assignee: Wacker-Chemie GmbH, Munich, Fed. Rep. of Germany

[21] Appl. No.: 26,834

[22] Filed: Mar. 17, 1987

[30] Foreign Application Priority Data

Apr. 8, 1986 [DE] Fed. Rep. of Germany ....... 3611760

[51] Int. Cl.$^4$ ............................................. C07C 45/63
[52] U.S. Cl. .................................. 568/437; 568/425; 568/495
[58] Field of Search ..................... 568/425, 437, 495

[56] References Cited

U.S. PATENT DOCUMENTS 4,051,168  9/1977  Feiring .
4,691,062  9/1987  Andrade et al. .................... 568/495

FOREIGN PATENT DOCUMENTS 6104832  9/1981  Japan ................................. 568/437

OTHER PUBLICATIONS

Baker, "J. Chem. Sci." (1956), p. 404.
Syper et al., "Synthesis", 1984, p. 747.
Drefahl et al., "Chem. Ber.", vol. 94, p. 907 (1961).
Theilheimer's Synthetic Methods of Organic Chemistry, vol. 39, p. 37, 1985.
Houden-Weyl, "Methoden der Organischen Chemie", vol. V/3, p. 835, 1962.
Patent Abstracts of Japan, vol. 3, No. 147, 1979.

*Primary Examiner*—Werren B. Lone
*Attorney, Agent, or Firm*—Collard, Roe & Galgano

[57] ABSTRACT

A process for the preparation of 4-chloromethylbenzaldehyde, 4-bromomethylbenzaldehyde and 4-iodomethylbenzaldehyde is disclosed. The desired 4-halomethylbenzaldehyde is prepared by reacting 4-hydroxymethylbenzaldehyde with the appropriate gaseous hydrogen halide and/or with the appropriate aqueous hydrohalic acid. The 4-halomethylbenzaldehydes produced by the disclosed process are useful as raw materials for pharmaceuticals and serve as starting materials for the preparation of conductive organic compounds.

13 Claims, No Drawings

PROCESS FOR THE PREPARATION OF 4-HALOMETHYLBENZALDEHYDE

The invention relates to the preparation of 4-halomethylbenzaldehyde; the halogen being chlorine, bromine or iodine. 4-Halomethylbenzaldehydes are used as raw materials for pharmaceuticals and serve as starting substances for the preparation of conductive organic compounds.

Several processes for the preparation of 4-halomethylbenzaldehydes are known. J. Baker et al. (*J. Chem. Soc.* 1956, 404) describe the reaction of 4-chloromethylbenzonitrile with $SnCl_2$ and hydrogen chloride to give 4-chloromethylbenzaldehyde and the reaction of 4-hydroxymethylbenzaldehyde with $PBr_3$ to give 4-bromomethylbenzaldehyde. This reference also describes the reaction of 4-chloromethylbenzaldehyde with KI to give 4-iodomethylbenzaldehyde. 4-Bromomethylbenzaldehyde can be prepared, according to J. Syper et al. (*Synthesis* 1984, 747) by oxidation of 4-bromomethylbenzyl chloride with selenium dioxide or, according to European Patent Application No. 45,150, by reduction of 4-bromomethylbenzoyl chloride with lithium tri-tert.-butoxyaluminum hydride. Moreover, G. Drefahl and G. Plöttner (*Chem. Ber.* 94, 907 (1961)) describe a synthesis in which tolylaldehyde is reacted with red phosphorus and bromine to give 4-bromomethylbenzal bromide which is then hydrolyzed with oxalic acid to 4-bromomethylbenzaldehyde. In addition, R. Grice and G. Owen (*J. Chem. Soc.* 1963, 1947) describe a method in which 4-methoxycarbonylbenzal-dimethylacetal is reduced with lithium aluminum hydride to 4-hydroxymethylbenzaldimethylacetal, whereupon the latter is converted to 4-chloromethylbenzaldehyde by treatment with gaseous HCl and subesequent reaction with thionyl chloride.

Disadvantageously, none of these processes is universally applicable, i.e., for obtaining the chloro-, bromo- and iodo- derivative from a single starting compound by the addition of simple base chemicals. Moreover, these processes use additives which, either cause considerable environmental pollution and high risk potentials, e.g., $SeO_2$, red phosphorus, bromine, chlorine or thionyl chloride, or, during the reaction, lead to by-products such as, for example, metal salts or sulfur dioxide, which must be separated off at great expense and also entail significant disposal problems.

It is an object of the present invention to avoid the foregoing disadvantages resulting from processes known to the art by providing a relatively simple, safe and economical process for the preparation of 4-halomethylbenzaldehydes.

The foregoing and related objects are achieved by a process for the preparation of 4-halomethylbenzaldehyde, the halogen being chlorine, bromine or iodine, which comprises the step of reacting 4-hydroxymethylbenzaldehyde with the appropriate gaseous hydrogen halide and/or with the appropriate aqueous hydrohalic acid.

The advantages of the process according to the invention are, in particular, that, starting from inexpensive base chemicals, 4-chloro-, 4-bromo- and 4-iodomethylbenzaldehyde can be prepared in good yields from a single starting compound in simple reaction apparatus, without expensive purification steps being necessary or by-products being obtained, the disposal of which are difficult. Further, the disadvantages of the state of the art are avoided.

Terephthaldialdehyde is readily obtainable by catalytic oxidation of p-xylene (G. D. Brindell et al., *Ind. Eng. Chem. Prod. Res. Dev.* 15(1), 83, 1976) or by dehydrogenation of p-xylylene glycol (U.S. Pat. No. 4,239,703).

The reduction of terephthaldialdehyde to 4-hydroxymethylbenzaldehyde can be carried out in any suitable manner presently known to the art, for example, in a manner analogous to that described in N. M. Weinschenker et al. (*J. Org. Chem.* 40, 1966, 1975), by reaction in toluene with a polymeric organo-tin hydride reagent, wherein n-butyl-tin dihydride groups are bonded to a polystyrene matrix, or analogously to G. D. Brindell et al. (*Ind. Eng. Chem., Prod. Res. Dev.* 1, 83, 1976) by reaction with hydrogen and palladium on active charcoal in aqueous ethanol, this being incorporated herein by reference with respect to further details in connection with the reduction. The reduction according to G. D. Brindell et al. is preferred. The crude 4-hydroxymethylbenzaldehyde product, which is obtained by this reaction and can still contain 1 to 5% of terephthaldialdehyde and 2 to 10% of 1,4-bis-hydroxymethylbenzene, is preferably used without further purification steps.

In the conversion of 4-hydroxymethylbenzaldehyde, the hydrogen halide is used, according to the invention, in the gaseous form or dissolved in water. In the case of aqueous hydrohalic acids, dilute solutions, for example 1 N hydrohalic acid, or concentrated solutions up to, for example, 12 N HCl, 8 N HBr and 7 N HI, can be employed. Preferably, concentrated hydrohalic acids are used.

The hydrogen halides used according to the invention are hydrogen chloride, hydrogen bromide or hydrogen iodide.

The molar ratio of 4-hydroxymethylbenzaldehyde and hydrogen halide, in the gaseous form or in aqueous solution, is preferably 1:1 to 1:10, more preferably 1:2 to 1:5 and especially, 1:3 to 1:4.

4-Hydroxymethylbenzaldehyde is employed as the melt, in an aqueous medium or in a solvent. The solvents used are inert, water-immiscible solvents, for example chlorinated hydrocarbons, e.g., chloroform or methylene chloride, or, for example, aromatics, such as, toluene.

In a preferred embodiment of the process according to the invention, gaseous hydrogen halide is passed for a period of, preferably 1 to 10 hours, and, in particular 2 to 5 hours, through a melt of 4-hydroxymethylbenzaldehyde or through a water-immiscible solution of 4-hydroxymethylbenzaldehyde. Preferably, the hydrogen halide is circulated in this case with any entrained water of the reaction being separated off by known methods. Such methods include, for example, condensing the entrained water out via inter-cooling of the circulating gas, adsorption on a drying agent, for example silica gel, or by washing out with concentrated sulfuric acid or phosphorus pentoxide, before recycling the hydrogen halide to the reaction. With the introduction of the hydrogen halide into the melt, the reaction temperature is preferably 80° to 200° C., more preferably 100° to 160° C. and especially 120° to 140° C. With introduction into a solution, the reaction temperature is preferably 0° to 100° C., and most preferably 40° to 80° C.

The water formed during reaction is carried over with the hydrogen halide or separated out from the water-immiscible solvent together with any unconsumed hydrogen halide as a concentrated hydrohalic acid.

In a further preferred embodiment of the process according to the invention, 4-hydroxymethylbenzaldehyde is reacted with an aqueous hydrohalic acid and, optionally, with the addition of a water-immiscible solvent. If desired, the hydrogen halide content can, at this point, be increased by introducing additional gaseous hydrogen halide. In this case, the reaction temperature is preferably 0° to 100° C., most preferably, 40° to 80° C. The reaction time is preferably 1 to 24 hours, most preferably 2 to 6 hours. In the case of a reaction with aqueous hydrohalic acid without added solvent, the product crystallizes out directly. In the case of a reaction with aqueous hydrohalic acid with an added water-immiscible solvent, the product is extracted by the solvent from the aqueous phase. The reaction product is then, preferably, extracted by the counter-current method in a manner known to those skilled in the art. The dilute hydrohalic acid obtained after the reaction can be reconcentrated by known measures, for example by distillation.

The present invention will now be described in greater detail by reference to the following examples. It should, however, be pointed out the examples are only illustrative of the present invention and are not intended to define the limitations or scope of the invention.

EXAMPLE 1

20 g of terephthaldialdehyde (0.149 moles) and 100 mg of Pd/C (10% Pd on active charcoal) were suspended in 100 ml of 80 percent ethanol under argon in a 500 ml three-necked flask. The flask was provided with a gas-tight stirrer seal and a blade stirrer. After the argon had been displaced by hydrogen, the mixture was vigorously stirred until the theoretical quantity of hydrogen (3.34 liters) had been absorbed. After evacuation for removal of the hydrogen, the catalyst was filtered off with suction. From the solution evaporated at 60° C. in a rotary evaporator, 20.5 g of crude product were obtained which contained 90 mole-% of 4-hydroxymethylbenzaldehyde, 5 mole-% of unconverted terephthaldialdehyde and 5 mole-% of 1,4-bis-hydroxymethylbenzene.

EXAMPLE 2

94.4 g of 4-hydroxymethylbenzaldehyde (90 percent pure, with 1,4-bis-hydroxymethylbenzene and terephthaldialdehyde as impurities) were introduced into a 250 ml three-necked flask with a magnetic stirrer and a gas inlet tube reaching down to the bottom. HCl gas was passed into the molten mass, the temperature rising to 75°. After HCl had been passed through for 2 hours, the mixture was heated to 140° C. in an oil bath and HCl was passed through for a further 2½ hours. Distillation at 17 mm Hg (boiling point 136° C.) gave 88.6 g of a white crystalline product which, according to NRM, contained 87.5% by weight of 4-chloromethylbenzaldehyde, 10.2% by weight of 1,4-bis-chloromethylbenzene and 2.3% by weight of terephthaldialdehyde. As the residue, 14.5 g of a viscous, non-volatile mass remained, into which HCl was again introduced for 1.5 hours at room temperature and then for 1.5 hours at 150° C.

After this treatment, it was possible to distill another 6.5 g of 95% pure 4-chloromethylbenzaldehyde out of this residue. Total yield, calculated on pure aldehyde was 83.7 g corresponding to 86.8% of the theoretical yield, relative to the pure aldehyde content of the starting material. $^H$NMR: 4.64 s 2H; 7.57 d 2H; 7.89 d 2H, J=8 Hz; 10.03 s 1H.

EXAMPLE 3

33 ml of 48 percent hydrobromic acid (0.29 moles) were added at room temperature to 20 g (0.132 moles) of 90 percent pure 4-hydroxymethylbenzaldehyde, with 1% of terephthaldialdehyde and 9% of 1,4-bis-hydroxymethylbenzene as impurities, and the mixture was then stirred for 2 hours at 65° C. After 18 hours at 4° C. in a refrigerator, the crystal mass was filtered off with suction, washed with 5 ml of 48 percent HBr and dried in a desiccator over phosphorus pentoxide. Crude yield: 16.8 g. Content according to NMR: 85.9% by weight corresponding to 54% of the theoretical yield of 4-bromomethylbenzaldehyde. $^H$NMR: 4.51 2H; 7.55 d 2H; 7.85 d 2H, J=8 Hz; 10.01 s 1 H.

EXAMPLE 4

66 g of 57 percent hydriodic acid (0.29 moles) were added to 20 g (0.132 moles) of 4-hydroxymethylbenzaldehyde (90 percent pure) and the mixture was kept for 2 hours under argon at 80° C., the product already crystallizing out and the batch solidifying to a solid mass. After standing at 4° C. for an additional 16 hours, the excess hydriodic acid was removed by filtration with suction and the product was dried over phosphorus pentoxide. The still slightly moist crude product (42.5 g) was, first, freed from moisture and iodine impurities in a sublimation apparatus at 0.005 mm Hg and 60° C., and then purified by sublimation at 95° C. This gave 26.14 g of sublimed product (still colored slightly brown due to a small iodine content) which contained 83% by weight of 4-iodomethylbenzaldehyde. The yield calculated on pure aldehyde was 21.7 g corresponding to 66% of the theoretical yield. As the sublimation residue, 5.2 g of a dirty-green powder remained, which was no longer soluble in chloroform. The second sublimation left about 350 mg of residue. 20.81 g of sublimed product with 88% of 4-iodomethylbenzaldehyde were obtained, which was contaminated with 1,4-bis-iodomethylbenzene and terephtaldialdehyde. After two recrystallizations from 400 ml of cyclohexane each time, 13 g of 4-iodomethylbenzaldehyde of 99% purity were obtained. $^H$NMR: 4.41 s 1H; 7.45 d 2H; 7.68 d 2H, J=8 Hz; 9.91 s 1H.

EXAMPLE 5

20 g (0.132 moles) of 90 percent pure 4-hydroxymethylbenzaldehyde were stirred for 2 hours at 80° C. under an argon atmosphere with 50 ml of 37 percent HCl (0.58 moles) and 200 ml of toluene. After cooling to room temperature, the aqueous phase was separated off and the toluene phase was evaporated in vacuo. This gave 16.2 g of crude product which, according to NMR, contained 78.8% by weight of 4-chloromethylbenzaldehyde, 10% by weight of 1,4-bis-chloromethylbenzene and 11.2% by weight of an unknown substance. A 4-chloromethylbenzaldehyde yield of 12.8 g, corresponding to 62.5% of the theoretical yield was calculated from the NMR result.

EXAMPLE 6

40 g (0.264 moles) of 90 percent pure 4-hydroxymethylbenzaldehyde were stirred for 2 hours at 80° C. with 132 ml of 48 percent HBr (1.17 moles) and 250 ml of toluene. The aqueous layer was separated off while still warm, whereupon the toluene solution was left to stand for 18 hours at 4° C. The crystals which had then precipitated were filtered off with suction, rinsed with a small amount of toluene and dried at 40° C. under 0.1 mm Hg. Yield: 36.85 g of 90 percent pure 4-bromomethylbenzaldehyde, contaminated with 1,4-bis-bromomethylbenzene. The mother liquor, after evaporation of the solvent and drying in a waterpump vacuum at 40° C. and 0.1 mm Hg, gave a further 20 g which, according to NMR, contained 68% of 4-bromomethylbenzaldehyde. Total yield relative to pure 4-bromomethylbenzaldehyde was 46.4 g corresponding to 88% of the theoretical yield.

EXAMPLE 7

According to Example 6, 17.13 g of 84 percent pure 4-hydroxymethylbenzaldehyde (0.106 moles) (remaining impurity: 10% of 1,4-bis-hydroxymethylbenzene+5% of terephthaldialdehyde) were reacted with 38.8 ml of 57 percent hydriodic acid (0.294 moles). After standing at 4° C., 24.7 g of crude product, which were immediately sublimed at 90° C. and 0.01 mm Hg without further drying, were obtained from the organic layer. This gave 21.95 g of sublimed product which, according to NMR, contained 88.8 mole-% of 4-iodomethylbenzaldehyde. By evaporation of the organic mother liquor in a waterpump vacuum and drying at 50° C. and 0.1 mm Hg, a second fraction with 68.5 mole-% of 4-iodomethylbenzaldehyde was obtained. This gives a calculated total 4-iodomethylbenzaldehyde yield of 23.6 g corresponding to 89% of the theoretical yield.

While only several examples of the present invention have been described, it will be obvious to those skilled in the art that many modifications may be made thereunto without departing from the spirit and scope of the invention.

What is claimed is:

1. A process for the preparation of a 4-halomethyl-benzaldelhyde, the halogen being chlorine, bromine or iodine, comprising the step of:
reacting 4-hydroxymethylbenzaldehyde with a hydrogen halide selected from the group consisting of gaseous hydrogen chloride, aqueous hydrochloric acid, a combination of gaseous hydrogen chloride and aqueous hydrochloric acid, gaseous hydrogen bromide, aqueous hydrobromic acid, a combination of gaseous hydrogen bromide and aqueous hydrobromic acid, gaseous hydrogen iodide, aqueous hydriodic acid and a combination of gaseous hydrogen iodide and aqueous hydriodic acid.

2. The process according to claim 1, wherein a water-immiscible solvent is added during said reacting step.

3. The process according to claim 2, wherein said water-immiscible solvent is a member selected from the group consisting of a chlorinated hydrocarbon and an aromatic.

4. The process according to claim 3, wherein said water-immiscible solvent is a member selected from the group consisting of chloroform, methylene chloride, toulene and a combination thereof.

5. The process according to claim 1, wherein said hydrogen halide is in a concentrated form and selected from the group consisting of aqueous hydrochloric acid, aqueous hydrobromic acid and aqueous hydriodic acid.

6. The process according to claim 5, wherein said hydrogen halide is hydrochloric acid having a concentration of 1 N to 12 N.

7. The process according to claim 5, wherein said hydrogen halide is hydrobromic acid having a concentration of 1 N to 8 N.

8. The process according to claim 5, wherein said hydrogen halide is hydriodic acid having a concentration of 1 N to 7 N.

9. The process according to claim 1, wherein the molar ratio of 4-hydroxymethylbenzaldehyde to said hydrogen halide is 1:1 to 1:10.

10. The process according to claim 9, wherein the molar ratio of 4-hydroxymethylbenzaldehyde to said hydrogen halide is 1:3 to 1:4.

11. The process according to claim 1, wherein 4-hydroxymethylbenzaldehyde is reacted in a molten state with said hydrogen halide selected from the group consisting of gaseous hydrogen chloride, gaseous hydrogen bromide and gaseous hydrogen iodide.

12. The process according to claim 11, wherein the reaction temperature is 80° to 200° C.

13. The process according to claim 12, wherein the reaction temperature is 120° to 140° C.

* * * * *